(12) United States Patent
Lapenna

(10) Patent No.: US 8,057,755 B2
(45) Date of Patent: Nov. 15, 2011

(54) CONSTRUCTIVE DISPOSITION APPLIED TO SAMPLE COLLECTOR FOR THE PURPOSES OF FECES PARASITOLOGICAL EXAM

(76) Inventor: José Carlos Lapenna, Itú (BR)

( * ) Notice: Subject to any disclaimer, the term of this patent is extended or adjusted under 35 U.S.C. 154(b) by 896 days.

(21) Appl. No.: 12/009,117

(22) Filed: Jan. 16, 2008

(65) Prior Publication Data

US 2008/0210619 A1 Sep. 4, 2008

(30) Foreign Application Priority Data

Feb. 12, 2007 (BR) .................................. 8700248 U

(51) Int. Cl.
*G01N 21/75* (2006.01)
*E21B 49/10* (2006.01)

(52) U.S. Cl. ..................................... 422/427; 73/152.25

(58) Field of Classification Search ................... 422/427; 73/152.25
See application file for complete search history.

(56) References Cited

U.S. PATENT DOCUMENTS

| 4,559,837 A * | 12/1985 | Cerqueira ................... 73/863.23 |
| 5,916,521 A * | 6/1999 | Bunce et al. ................... 422/422 |
| 7,648,681 B2 * | 1/2010 | Meyer et al. ................... 422/547 |
| 7,871,574 B2 * | 1/2011 | Peltier .......................... 422/536 |

FOREIGN PATENT DOCUMENTS

| BR | MU 8402055-5 | 4/2006 |
| WO | WO 2006/017917 | 2/2006 |

* cited by examiner

*Primary Examiner* — Lore Jarrett
(74) *Attorney, Agent, or Firm* — Collard & Roe, P.C.

(57) ABSTRACT

The present application is about a new construction disposition applied to sample collector for the purposes of feces parasitological exams, more precisely to one new construction form which is manufactured with a reduced number of parts, helping with its low cost, since it is a product discharged after its utilization; collector which includes a container which receives the attachment of a cover which contemplates a central conic sector from whose top a cylindrical duct is developed which can be closed by an over-cover or cap; it is predicted a concave filtering element, formed by polyester net or mesh in the order of 220 to 280μ, preferably 266μ, which represents the same radius of internal bending of the conic portion of the cover, affixed to it by means of fitting or another equivalent mean.

2 Claims, 3 Drawing Sheets

FIG.1
FIG.2
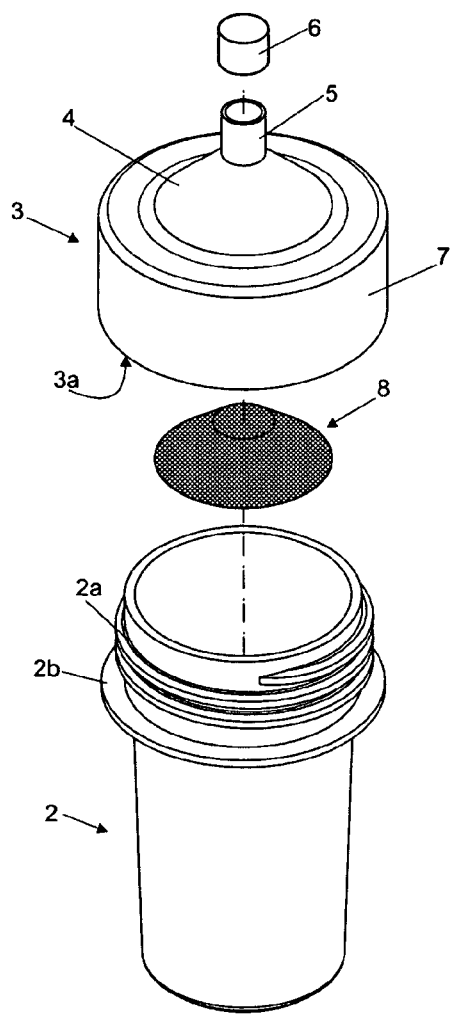
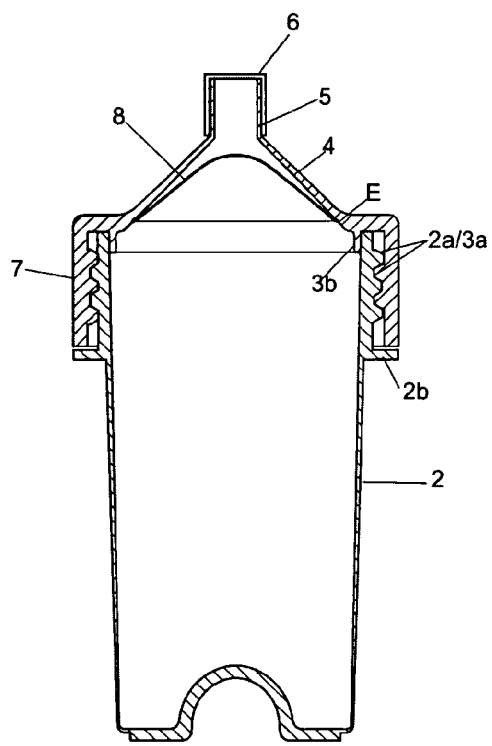

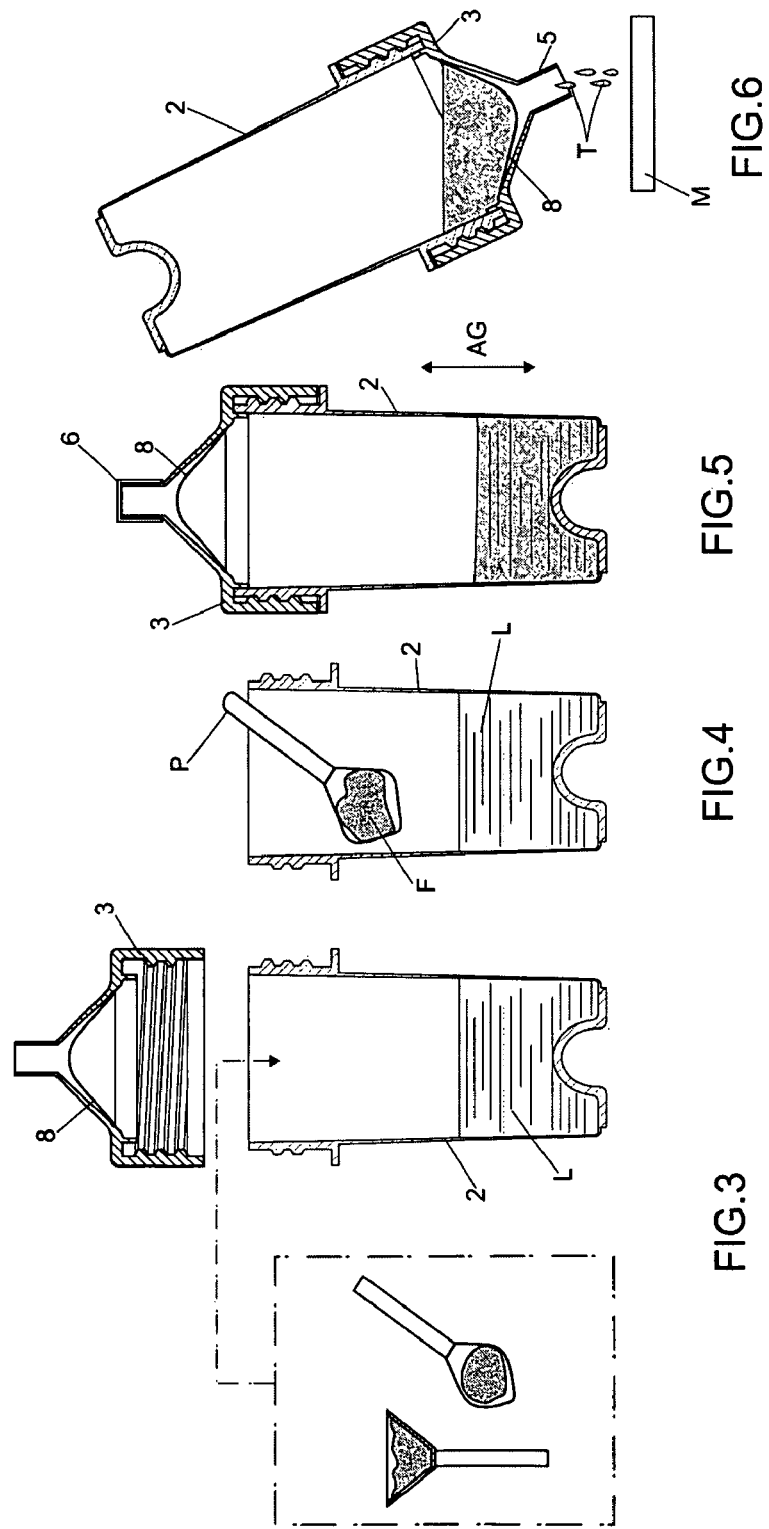

CONSTRUCTIVE DISPOSITION APPLIED TO SAMPLE COLLECTOR FOR THE PURPOSES OF FECES PARASITOLOGICAL EXAM

FIELD OF THE INVENTION

The present application is about the use of one new constructive disposition applied to sample collector for the purposes of feces parasitological exam more precisely to one new constructive form which aims to ease the laboratorist work during the whole collection, transportation, dilution and filtering operation, so as to obtain the sample in the own shaking container, dripping, at the end some drops on the blade for the microscopic exam; said new collector is presented manufactured in a reduced number of parts, which results in its low cost, since it is about a product discharged after its utilization.

BACKGROUND OF THE INVENTION

In a general sense, the feces parasitological exams, performed in clinic analysis laboratories are based in a procedure which includes since the material collection to its filtering in order to obtain a sample to be forwarded to the analysis equipment.

Currently, it is known that the sample is obtained from conic filtering elements, conformed by one high density polyethylene net whose weft presents the order of 500μ. Even if being a mesh with dimensionally acceptable weft, it is not considered ideal yet for the sample obtainment, and it fails as regards reliability on the analysis process.

This occurs because the polyethylene mesh presents a variation as regards the correct weft spacing, imperfection which occurs during the mesh injecting process, resulting in whole areas without perforation, affecting the element filtering performance.

Another factor of high importance concerns the bio-safety concept related to the clinic analysis field, once the material treated is highly infectious, and may carry risks to the professional handling it.

PRIOR ART

The present request claimant has already filed an application under number MU 8402055-5, where an enhanced collector is presented, with a constructive concept distinct from those in the conventional market and where it was projected one container in the shape of a bottle, in whose interior a filtering element is assembled with side portion formed by weft polyester frame in the order of 150 to 300μ, and which has, in its lower portion, an element in the shape of rod to which end the collector is applied from where the filtered material precipitates and accommodates in the grooves or holes, remaining further immersed in conservation liquid. Such construction has been successful as regards the procedure in clinic analysis laboratories, because it synthesizes the feces parasitological exam, since its collection, passing through the conservation, dilution, filtering, and providing sediment highly clean for the microscopic analysis; it performs many more exams in a reduced physical space and time at an extremely low cost.

SUMMARY OF THE INVENTION

Therefore, the claimant, operating in the area and concerned in improving even more the parasitological exam quality, conceived a new collector model which adds improvements to the model mentioned above, since it effectively benefits not only the laboratorist work but also the obtained result.

The now innovated collector is made up with a reduced number of parts, which represents lower cost in relation to the remaining ones in the market. Therefore, the collector comprises a recipient body with capacity around 35 ml, a cover contemplating a central conic sector covered by a cylindrical duct where the over cover or cap is attached and a lower cylindrical sector with internal thread, which may be attached to the recipient body nozzle. A concave filtering element is projected, formed by polyester net or mesh in the order of 220 to 280μ, preferably 266μ, which is affixed to the internal surface of the cover conic portion by means of fitting or another proper mean.

Such construction keeps the excellence of the filtering of the material to be analyzed, in relation to the previously described one, and brings further a reduced cost solution, since such collection devices must be discharged after its use.

BRIEF DESCRIPTION OF THE DRAWINGS

So as to complement the present description to obtain a better understanding of the utility model features and according to its practical performance preference, it can be found attached to the description a group of drawings which in an exemplified way, although not limited, the following was represented:

FIG. 1 represents a collector burst perspective, according to its favorite embodiment, depicting the assembly components;

FIG. 2 shows one section of the assembled collector, according to what is presented in FIG. 1;

FIGS. 3 to 6 display the now claimed collector utilization sequence;

DETAILED DESCRIPTION OF THE INVENTION

Figure 8:
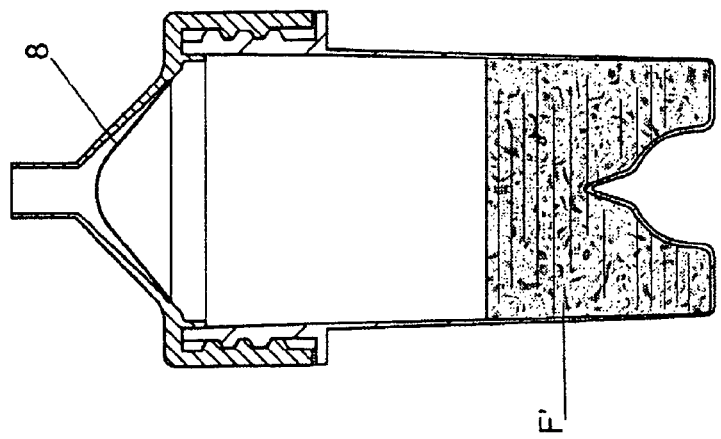
FIGS. 7 and 8 represent a construction variation of the container with a shovel, designed for a certain kind of material.

As regards the depicted drawings, the present embodiment refers to a new constructive disposition applied to sample collector for the purposes of feces parasitological exam, more precisely of one collector 1 which includes a container 2, with capacity around 35 ml, preferably in cylindrical format, whose top external portion is provided with thread 2a and flange 2b; said thread 2a receives attachment from one cover 3 through thread 3a and owns, as sealing element between parts 2 and 3, a surrounding ring 3b.

According to the present model of utility, the cover 3 contemplates a central conic sector 4 from which top a cylindrical duct is developed 5 which can be closed with over-cover or cap 6; from the conic sector biggest base 4, said cover develops a cylindrical sector 7, where the internal thread is practiced 3a.

The collector 1 predicts a concave filtering element 8, formed by polyester net or mesh in the order of 220 to 288μ, preferably 266μ, element which presents a semi-accompaniment of the conic portion internal bending 4 at the cover, affixed to it by means of fitting into cavity E especially designed to receive and accommodate safely the element 8 so as to keep the net edge affixed to the cover internal face.

The collector utilization form, represented in FIGS. 3 to 6, shows that the container 2, already supplied with conservation liquid L, is separated from the cover so as to receive a portion of feces F, collected with a shovel P, of any format.

And then the container 2 is closed by the cover, still closed by the over-cover 6; from there the collector is shaken AG until the portion of feces is diluted into the liquid L.

Done that, the over-cover is removed and the collector is turned so as to allow that some drops T of the dilution obtained may be filtered by the filtering element 8, and forwarded, through blades M, to the proper clinic analysis.

Figure 7:
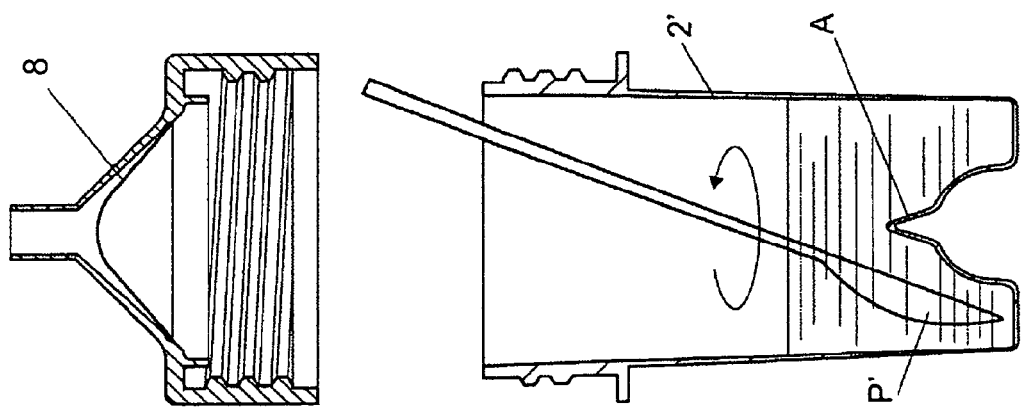

In a construction variation, FIGS. 7 and 8, more particularly applied to the case of feces of the hardened kind, which usually produces poor samples due to the lack of dilution, it is verified that the container bottom 2' contemplates a funneled extension A, which will serve as the scratching mean and support for the feces sample removal F' from the shovel P', format which allows to macerate the feces sample F' until its complete dilution, solving thus the problem concerning poor samples due to lack of dilution.

While it is described the preferred performance of the present utility model, any modifications and/or changes must be understood as within the utility model scope, and must fit perfectly to the criteria defining the model, that is to say, the combination and modification of already known elements in new format or disposition, resulting in functional improvement in its use or manufacture.

The invention claimed is:

1. A sample collector for feces parasitological exams, comprising:
   a cylindrical container having a threaded portion on an upper end thereof and a flange;
   a lid comprising a conical central sector from which a cylindrical duct arises, and a cylindrical sector with an internal thread, at a base of the conical central sector;
   a cap closing the cylindrical duct;
   a sealing ring element between the lid and the flange; and
   a concave filtering element made of a polyester mesh with 220μ to 280μ, wherein said filtering element is spaced from the lid by a gap, and is fitted in an internal position of the lid by having the filtering element curved inwards along a contour of the lid.

2. The sample collector according to claim 1, wherein a bottom of the container is provided with an internal funneled-shaped protrusion.

* * * * *